United States Patent
Yamamoto

(10) Patent No.: US 10,426,323 B2
(45) Date of Patent: Oct. 1, 2019

(54) OBJECTIVE LENS FOR ENDOSCOPES AND ENDOSCOPE

(71) Applicant: FUJIFILM Corporation, Tokyo (JP)

(72) Inventor: Chikara Yamamoto, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 337 days.

(21) Appl. No.: 15/391,206

(22) Filed: Dec. 27, 2016

(65) Prior Publication Data

US 2017/0224201 A1    Aug. 10, 2017

(30) Foreign Application Priority Data

Feb. 8, 2016   (JP) ................................ 2016-021979

(51) Int. Cl.
| | |
|---|---|
| *A61B 1/00* | (2006.01) |
| *G02B 23/24* | (2006.01) |
| *G02B 27/00* | (2006.01) |
| *G02B 9/04* | (2006.01) |

(52) U.S. Cl.
CPC ............ *A61B 1/00163* (2013.01); *G02B 9/04* (2013.01); *G02B 23/243* (2013.01); *G02B 27/005* (2013.01)

(58) Field of Classification Search
CPC ...... G02B 13/0035; G02B 13/18; G02B 9/12; G02B 13/04; G02B 13/06; G02B 13/0045; G02B 13/16; G02B 9/16; G02B 27/0025; G02B 13/22; G02B 13/004; G02B 13/006; G02B 9/34; G02B 23/243; G02B 3/04; G02B 13/00; G02B 13/0015; G02B 13/0085; G02B 13/02; G02B 15/163

See application file for complete search history.

(56) References Cited

U.S. PATENT DOCUMENTS

| | | | |
|---|---|---|---|
| 2002/0024746 A1 | 2/2002 | Hagimori | |
| 2008/0252997 A1* | 10/2008 | Duckett | G02B 23/243 359/753 |
| 2011/0069400 A1 | 3/2011 | Duckett, III | |
| 2011/0228410 A1* | 9/2011 | Hsu | G02B 13/0035 359/716 |

(Continued)

FOREIGN PATENT DOCUMENTS

| | | |
|---|---|---|
| JP | 2002-082284 A | 3/2002 |
| JP | 4846752 B2 | 12/2011 |
| JP | 5485482 B1 | 5/2014 |

OTHER PUBLICATIONS

An Office Action mailed by the Japanese Patent Office dated Mar. 5, 2019, which corresponds to Japanese Patent Application No. 2016-021979 and is related to U.S. Appl. No. 15/391,206.

*Primary Examiner* — Evan P Dzierzynski
*Assistant Examiner* — Sharrief I Broome
(74) *Attorney, Agent, or Firm* — Studebaker & Brackett PC

(57) ABSTRACT

The number of lenses within an objective lens for endoscopes is only three. The objective lens for endoscopes includes, in order from the object side, a first lens which is a single lens having a negative refractive power and a concave surface toward the object side, an aperture stop, and a cemented lens. The cemented lens is formed by cementing one positive lens and one negative lens together. Conditional formulae related to the distance from the surface toward the object side of the first lens to the aperture stop and the Abbe's numbers of the positive lens and the negative lens that constitute the cemented lens are satisfied.

14 Claims, 6 Drawing Sheets

EXAMPLE 1

(56) References Cited

U.S. PATENT DOCUMENTS

2013/0120859 A1* 5/2013 Tsai .................. G02B 13/0035
359/716
2014/0155694 A1* 6/2014 Murata ................ G02B 23/243
600/109

* cited by examiner

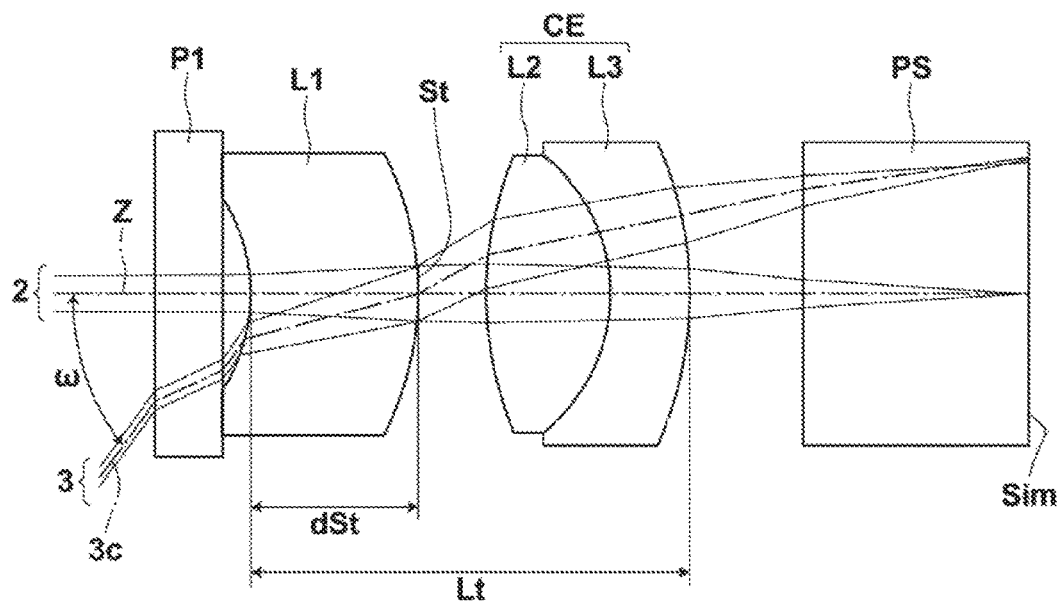
FIG.1 EXAMPLE 1
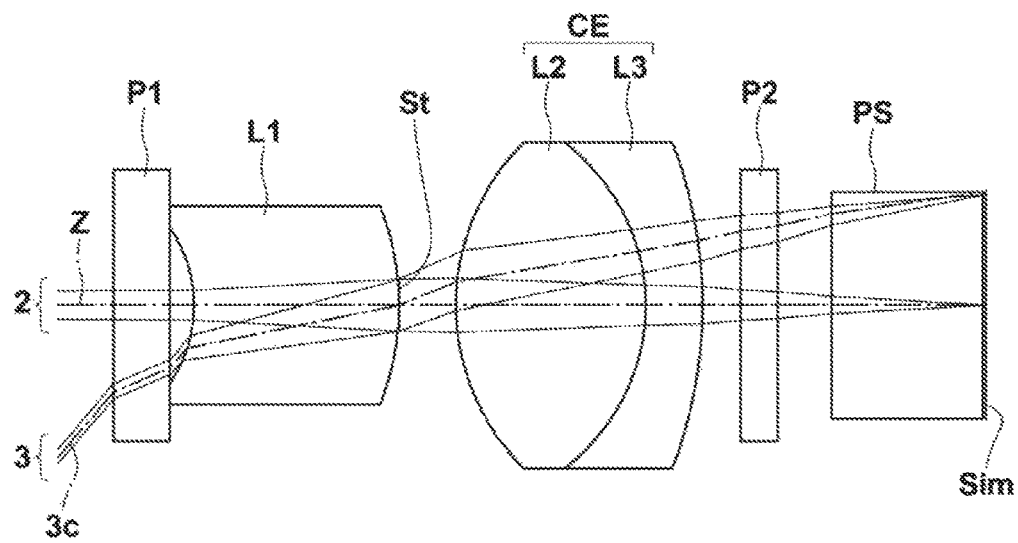
FIG.2 EXAMPLE 2

FIG.3 EXAMPLE 3
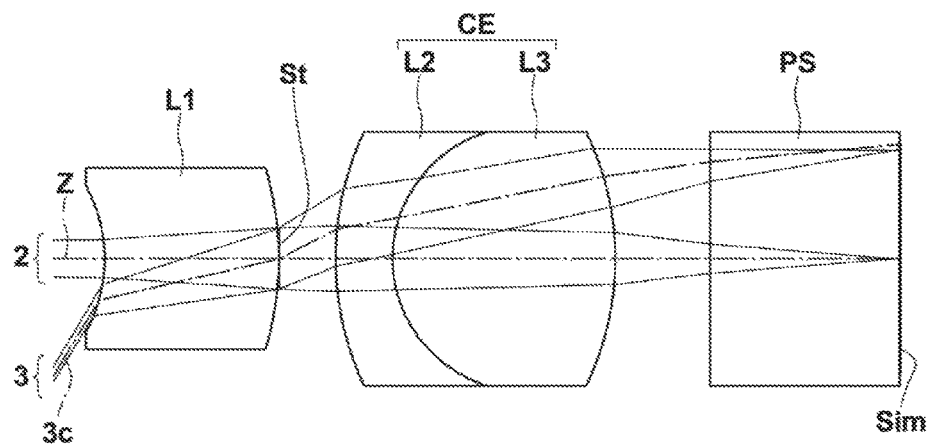

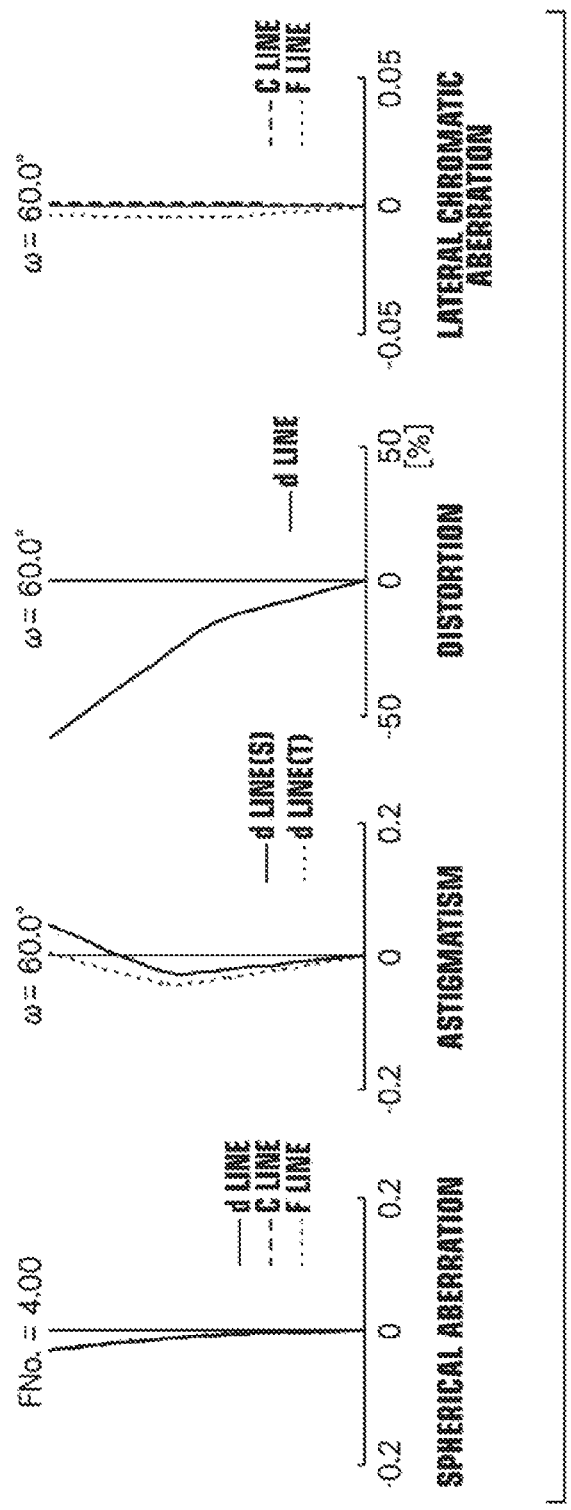

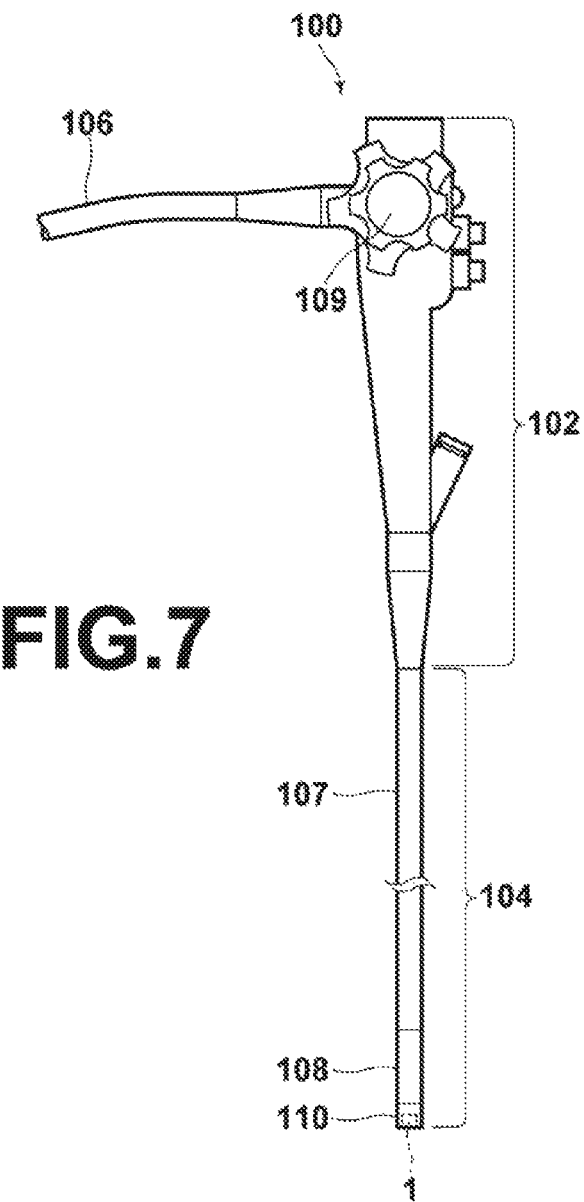

OBJECTIVE LENS FOR ENDOSCOPES AND ENDOSCOPE

CROSS REFERENCE TO RELATED APPLICATIONS

The present application claims priority under 35 U.S.C. § 119 to Japanese Patent Application No. 2016-021979 filed on Feb. 8, 2016. The above application is hereby expressly incorporated by reference in its entirety, into the present application

BACKGROUND

The present disclosure is related to an objective lens for endoscopes and to an endoscope.

Conventionally, endoscopes are employed to observe and treat the interiors of patients' bodies in the medical field. Objective lenses for use in endoscopes are disclosed in Japanese Patent No. 4846752 and Japanese Patent No. 5485482. Japanese Patent No. 4846752 discloses a lens system having a three lens configuration, which includes, in order from the object side to the image side, a negative lens, an aperture stop, a planoconvex lens having a convex surface toward the image side, and a planoconvex lens having a convex surface toward the object side. Japanese Patent No. 5485482 discloses a lens system having a three lens configuration, which includes, in order from the object side to the image side, an aperture stop, a positive lens, and a cemented lens.

SUMMARY

It is desired for endoscopes to become thinner in diameter and compact, in order to lessen the burden on patients. Therefore, it is desired for the number of lenses in objective lenses for endoscopes to be decreased, and for objective lenses for endoscopes to have compact configurations. Meanwhile, there is demand for objective lenses for endoscopes to favorably correct chromatic aberrations, in order to accurately find and/or diagnose lesions.

No data related to numerical values or properties related to aberrations are not explicitly disclosed with respect to the objective lens for endoscopes of Japanese Patent No. 4846752. However, because the objective lens for endoscopes disclosed in Japanese Patent No. 4846752 is of a configuration that does not employ a cemented lens, it is considered difficult to expect that chromatic aberrations can be favorably corrected. In the lens system disclosed in Japanese Patent No. 5485482, the aperture stop is positioned at the object side of the lens most toward the object side. Chromatic aberrations cannot be balanced between the object side and the image side of the aperture stop, and therefore it is difficult for chromatic aberrations to be sufficiently corrected.

The present disclosure has been developed based on the foregoing circumstances. The present disclosure provides an objective lens for endoscopes having a small number of lenses and a compact configuration, which corrects chromatic aberrations and has favorable optical performance. The present disclosure also provides an endoscope equipped with this objective lens for endoscopes.

An objective lens for endoscopes of the present disclosure comprises, in order from the object side to the image side:

a single lens having a negative refractive power and a concave surface toward the object side;

an aperture stop; and a cemented lens;

the cemented lens being formed by one positive lens and one negative lens which are cemented together;

the number of lenses within the entire system being only three; and

Conditional Formulae (1) and (2) below being satisfied:

$$0.1 < dSt/Lt < 0.6 \tag{1}$$

$$0 < vp - vn < 55 \tag{2}$$

wherein dSt is the distance along the optical axis from the surface toward the object side of the single lens to the aperture stop, Lt is the distance along the optical axis from the surface toward the object side of the single lens to the surface toward the image side of the cemented lens, vp is the Abbe's number with respect to the d line of the positive lens within the cemented lens, and vn is the Abbe's number with respect to the d line of the negative lens within the cemented lens.

It is preferable for at least one of Conditional Formulae (3) through (6), (1-1) through (6-1), and (3-2) below to be satisfied in the objective lens for endoscopes of the present disclosure.

$$1.0 < fce/f < 2.0 \tag{3}$$

$$1.5 < Lt/f < 5.0 \tag{4}$$

$$0.8 < Bf/f < 1.8 \tag{5}$$

$$90° < 2\omega \tag{6}$$

$$0.2 < dSt/Lt < 0.5 \tag{1-1}$$

$$10 < vp - vn < 45 \tag{2-1}$$

$$1.1 < fce/f < 1.7 \tag{3-1}$$

$$1.8 < Lt/f < 4.0 \tag{4-1}$$

$$1.0 < Bf/f < 1.5 \tag{5-1}$$

$$100° < 2\omega \tag{6-1}$$

$$1.2 < fce/f < 1.6 \tag{3-2}$$

wherein fce is the focal length of the cemented lens, f is the focal length of the entire lens system, Lt is the distance along the optical axis from the surface toward the object side of the single lens to the surface toward the image side of the cemented lens, Bf is the back focus of the entire lens system as an air converted distance, $2\omega$ is the maximum full angle of view, vp is the Abbe's number with respect to the d line of the positive lens within the cemented lens, and vn is the Abbe's number with respect to the d line of the negative lens within the cemented lens.

The objective lens for endoscopes of the present disclosure may be configured to have a plane parallel plate positioned at the most object side thereof.

An endoscope of the present disclosure is equipped with the objective lens for endoscopes of the present disclosure.

Note that the expression "single lens" refers to that which is constituted by one lens which is not cemented to another lens. In addition, the expression "the number of lenses within the entire system being only three" refers to essential components. The objective lens for endoscopes of the present disclosure may include lenses that do not have practical power. Note that hybrid aspherical lenses (lenses formed by a spherical lens and an aspherical film laminated on the spherical lens in order to function as aspherical lenses) are not considered to be cemented lenses, but are treated as single lenses.

Note that the symbols of the refractive powers and the surface shapes of the lenses above are those in the paraxial region for lenses that include aspherical surfaces. The conditional formulae above all use the d line (wavelength: 587.6 nm) as a reference. The sign of dSt above is positive for cases in which the surface toward the object side of the single lens is positioned at the object side of the aperture stop, and negative for cases in which the surface toward the object side of the single lens is positioned at the image side of the aperture stop.

According to the present disclosure, the configuration of each lens and the position of the aperture stop are favorably set in a lens system in which the number of lenses is three, and predetermined conditional formulae are satisfied. Therefore, an objective lens for endoscopes having a compact configuration and favorable optical performance that corrects chromatic aberrations, as well as an endoscope equipped with this objective lens for endoscopes, can be provided.

BRIEF DESCRIPTION OF THE DRAWINGS

FIG. 1 is a sectional diagram that illustrates the configuration of an objective lens for endoscopes of Example 1 of the present disclosure and the paths of light rays that pass therethrough.

FIG. 2 is a cross sectional diagram that illustrates the configuration of an objective lens for endoscopes of Example 2 of the present disclosure and the paths of light rays that pass therethrough.

FIG. 3 is a cross sectional diagram that illustrates the configuration of an objective lens for endoscopes of Example 3 of the present disclosure and the paths of light rays that pass therethrough.

FIG. 6 is a collection of diagrams that illustrate various aberrations of the objective lens for endoscopes of Example 3, which are spherical aberration, astigmatism, distortion, and lateral chromatic aberration in this order from the left side of the drawing sheet.

FIG. 7 is a diagram that illustrates the schematic structure of an endoscope according to an embodiment of the present disclosure.

DETAILED DESCRIPTION OF THE EMBODIMENTS

Figure 4:
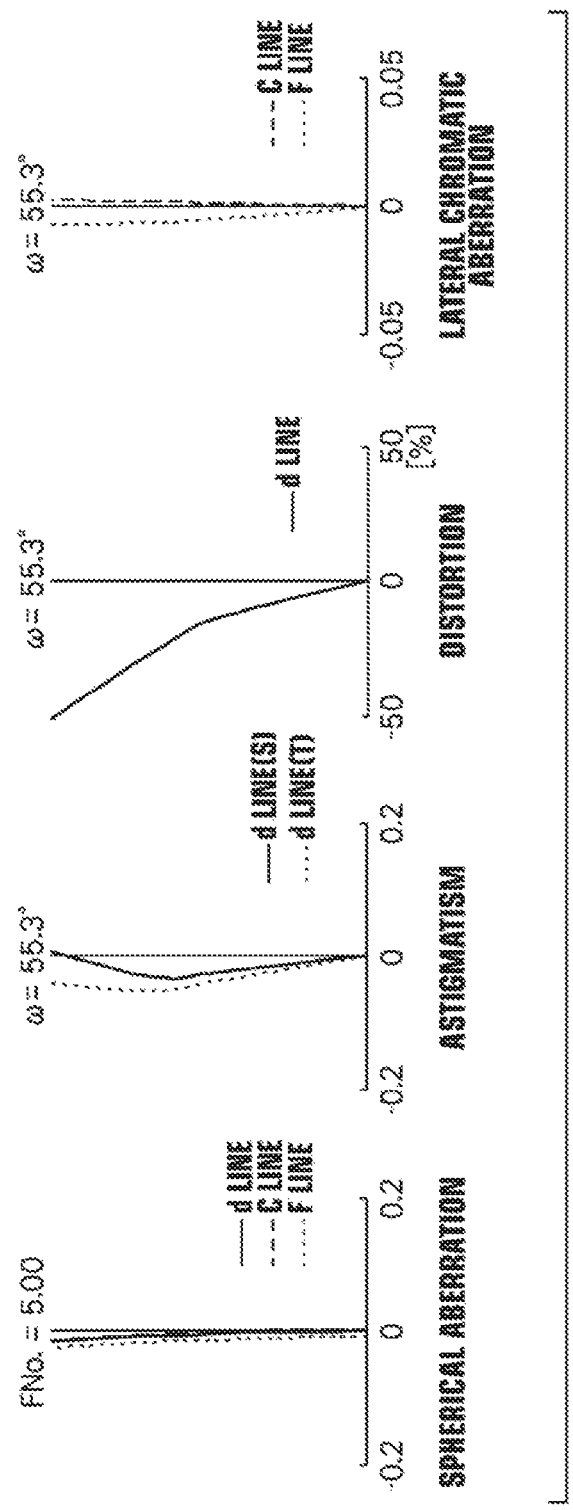
FIG. 4 is a collection of diagrams that illustrate various aberrations of the objective lens for endoscopes of Example 1, which are spherical aberration, astigmatism, distortion, and lateral chromatic aberration in this order from the left side of the drawing sheet.

Hereinafter, embodiments of the present invention will be described in detail with reference to the attached drawings. FIG. 1 through FIG. 3 are cross sectional diagrams that illustrate the configurations of and the paths of light rays that pass through objective lenses for endoscopes according to embodiments of the present disclosure which respectively correspond to Examples 1 through 3 to be described later. The basic configurations of the examples illustrated in FIG. 1 through FIG. 3 and the manners in which they are illustrated are the same. Therefore, a description will be given below with reference mainly to FIG. 1. In FIG. 1, the left side of the drawing sheet is the object side, the right side of the drawing sheet is the image side, and optical paths are illustrated for an axial light beam 2 and an off axis light beam 3 at a maximum angle of view.

This objective lens for endoscopes has, in order from the object side to the image side along an optical axis Z, a first lens L1, which is a single lens, an aperture stop St, and a cemented lens CE. Note that the aperture stop St which is illustrated in FIG. 1 does not necessarily represent the size and/or shape thereof, but the position thereof along the optical axis Z. This objective lens for endoscopes is configured such that the entire lens system, in which the number of lenses is only three. Thereby, the objective lens for endoscopes can be formed as a compact lens system.

Note that FIG. 1 illustrates an example in which a plane parallel plate P1 is positioned at the object side of the first lens L1, and a plane parallel optical member PS is positioned at the image side of the cemented lens CE. However, the plane parallel plate P1 and the optical member PS are not essential components of the present disclosure, and may be omitted. The plane parallel plate P1 will be described later. The optical member PS presumes a cover glass, various filters, an optical path converting prism for bending optical paths, etc. In the case that an optical path converting prism is employed, optical paths will become bent. However, FIG. 1 is a diagram in which optical paths are expanded, in order to facilitate understanding.

The first lens L1 of the objective lens for endoscopes is configured to be a lens having a negative refractive power and a concave surface toward the object side. By adopting such a shape, the outer radius of the first lens L1 can be decreased. In addition, positioning a negative lens most toward the object side is advantageous from the viewpoint of widening the angle of view.

The cemented lens CE is constituted by one positive lens and one negative lens, which are cemented together. Chromatic aberrations can be decreased by adopting this configuration. Note that FIG. 1 illustrates an example of the cemented lens CE in which a second lens L2, which is a positive lens, and a third lens L3, which is a negative lens, provided in this order from the object side to the image side, are cemented together. Alternatively, the cemented lens CE may be constituted by a negative lens and a positive lens, provided in this order from the object side to the image side, are cemented together, as illustrated in FIG. 3.

In this objective lens for endoscopes, the aperture stop St is positioned between the first lens L1 and the cemented lens CE. Thereby, chromatic aberrations can be balanced between the object side and the image side of the aperture stop St, which is advantageous from the viewpoint of reducing chromatic aberrations in a lens system having a wide angle of view.

The objective lens for endoscopes is configured such that Conditional Formulae (1) and (2) are satisfied.

$$0.1 < dSt/Lt < 0.6 \qquad (1)$$

$$0 < vp - vn < 55 \qquad (2)$$

wherein dSt is the distance along the optical axis from the surface toward the object side of the single lens to the aperture stop, Lt is the distance along the optical axis from the surface toward the object side of the single lens to the surface toward the image side of the cemented lens, vp is the Abbe's number with respect to the d line of the positive lens within the cemented lens, and vn is the Abbe's number with respect to the d line of the negative lens within the cemented lens.

By configuring the objective lens for endoscopes such that the value of dSt/Lt is not less than or equal to the lower limit defined in Conditional Formula (1), the thickness of the first lens L1 can be secured, and the strength of the first lens L1 can be prevented from being insufficient. By configuring the objective lens for endoscopes such that the value of dSt/Lt is not greater than or equal to the upper limit defined in Conditional Formula (1), the outer radius of first lens L1 can be suppressed from increasing. dSt is the distance along the optical axis from the lens surface most toward the object side to the aperture stop. Generally, objective lenses for endoscopes are wide angle lens systems, and increases in the radius of the lens most toward the object side become significant as dSt becomes longer in wide angle lens systems. Therefore, by configuring the objective lens for endoscopes such that the value of dSt/Lt is not greater than or equal to the upper limit defined in Conditional Formula (1), this increase in the radius can be suppressed, which is advantageous from the viewpoint of realizing a compact lens system. It is more preferable for Conditional Formula (1-1) below to be satisfied, in order to cause the advantageous effects related to Conditional Formula (1) to become more prominent.

$$0.2 < dSt/Lt < 0.5 \quad (1\text{-}1)$$

By selecting materials such that Conditional Formula (2) is satisfied, chromatic aberrations can be reduced. It is more preferable for Conditional Formula (2-1) below to be satisfied, in order to cause the advantageous effects related to Conditional Formula (2) to become more prominent.

$$10 < vp - vn < 45 \quad (2\text{-}1)$$

In addition, it is preferable for Conditional Formula (3) below to be satisfied in the objective lens for endoscopes.

$$1.0 < fce/f < 2.0 \quad (3)$$

wherein fce is the focal length of the cemented lens, and f is the focal length of the entire lens system.

By configuring the objective lens for endoscopes such that the value of fce/f is not less than or equal to the lower limit defined in Conditional Formula (3), favorable correction of aberrations is facilitated. By configuring the objective lens for endoscopes such that the value of fce/f is not greater than or equal to the upper limit defined in Conditional Formula (3), the total length of the entire length system can be shortened. It is more preferable for Conditional Formula (3-1) below to be satisfied, in order to cause the advantageous effects related to Conditional Formula (3) to become more prominent.

$$1.1 < fce/f < 1.7 \quad (3\text{-}1)$$

In addition, the lower limit of Conditional Formula (3-1) may be changed to 1.2, in order to cause the advantageous effects related to the lower limit of Conditional Formula (3-1) to become more prominent. Similarly, the upper limit of Conditional Formula (3-1) may be changed to 1.6, in order to cause the advantageous effects related to the upper limit of Conditional Formula (3-1) to become more prominent. It is further preferable for Conditional Formula (3-2) below, which is Conditional Formula (3-1) of which the lower limit and the upper limit are changed to these values, to be satisfied.

$$1.2 < fce/f < 1.6 \quad (3\text{-}2)$$

In addition, it is preferable for Conditional Formula (4) below to be satisfied in the objective lens for endoscopes.

$$1.5 < Lt/f < 5.0 \quad (4)$$

wherein Lt is the distance along the optical axis from the surface toward the object side of the single lens to the surface toward the image side of the cemented lens, and f is the focal length of the entire lens system.

By configuring the objective lens for endoscopes such that the value of Lt/f is not less than or equal to the lower limit defined in Conditional Formula (4), favorable correction of aberrations will be facilitated. By configuring the objective lens for endoscopes such that the value of Lt/f is not greater than or equal to the upper limit defined in Conditional Formula (4), an increase in the size of the lens system can be suppressed. It is more preferable for Conditional Formula (4-1) below to be satisfied, in order to cause the advantageous effects related to Conditional Formula (4) to become more prominent.

$$1.8 < Lt/f < 4.0 \quad (4\text{-}1)$$

In addition, it is preferable for Conditional Formula (5) below to be satisfied in the objective lens for endoscopes.

$$0.8 < Bf/f < 1.8 \quad (5)$$

wherein Bf is the back focus of the entire lens system as an air converted distance, and f is the focal length of the entire lens system.

By configuring the objective lens for endoscopes such that the value of Bf/f is not less than or equal to the lower limit defined in Conditional Formula (5), a space for positioning the optical member PS can be secured, and an amount of adjustment can be secured for the distance from the lens surface most toward the image side within the objective lens for endoscopes to an image formation position. By configuring the objective lens for endoscopes such that the value of Bf/f is not greater than or equal to the upper limit defined in Conditional Formula (5), an increase in the size of the lens system can be suppressed. It is more preferable for Conditional Formula (5-1) below to be satisfied, in order to cause the advantageous effects related to Conditional Formula (5) to become more prominent.

$$1.0 < Bf/f < 1.5 \quad (5\text{-}1)$$

In addition, it is preferable for Conditional Formula (6) below to be satisfied in the objective lens for endoscopes.

$$90° < 2\omega \quad (6)$$

wherein $2\omega$ is the maximum full angle of view.

In FIG. 1, the angle formed by the principal light ray 3c of the off axis light beam 3 and the optical axis Z is illustrated as the half value $\omega$ of the maximum full angle of view. By configuring the objective lens for endoscopes such that the value of $2\omega$ is not less than or equal to the lower limit defined in Conditional Formula (6), observation of a wide field of view which is desired in objective lenses for endoscopes will become possible. By enabling observation of a wide field of view, the amount of time required for observation can be shortened, and the amount of time that an endoscope is inserted within the body of a patient can be shortened. As a result, the burden on the patient can be lessened. It is more preferable for Conditional Formula (6-1) below to be satisfied, in order to cause the advantageous effects related to Conditional Formula (6) to become more prominent.

$$100° < 2\omega \quad (6\text{-}1)$$

The objective lens for endoscopes may be configured such that the plane parallel plate P1 formed by an optical material is positioned at the most object side thereof, as illustrated in FIG. 1. Generally, objective lenses for endoscopes are utilized while inserted within bodies. Therefore, there are cases in which liquids such as body fluids become adhered to the surface most toward the object side during utilization. The surface toward the object side of the first lens L1 in the objective lens for endoscopes of the present embodiment is a concave surface. Therefore, there is a possibility that liquid will remain in the concave surface if the concave surface is exposed to liquid. Therefore, by positioning the plane parallel plate P1 at the object side of the first lens L1, retention of liquid on the lens surface can be prevented. However, a configuration which is not equipped with the plane parallel plate P1 may be adopted when observing an organ within the human body in which body fluids are generally not present, for example, the lung.

Arbitrary combinations of the preferred configurations and the possible configurations described above are possible. It is preferable for the preferred configurations and possible configurations described above to be selectively adopted as appropriate, according to items required of the objective lens for endoscopes. According to the present embodiment, it is possible to realize an objective lens for endoscopes having a small number of lenses and a compact configuration, which corrects chromatic aberrations and has favorable optical performance.

Next, specific examples of numerical values of the objective lens for endoscopes of the present disclosure will be described. Note that all of the Examples below are normalized such that the focal length of the entire lens system is 1.00.

EXAMPLE 1

The lens configuration of and the paths of light beams through the objective lens for endoscopes of Example 1 are illustrated in FIG. 1. The manner in which the objective lens for endoscopes is illustrated has been described above, and redundant descriptions will be omitted here. The objective lens for endoscopes of Example 1 has, in order from the object side and the image side, the first lens L1 of a negative meniscus shape with a concave surface toward the object side, the aperture stop St, and the cemented lens CE formed by cementing the second lens L2 of a biconvex shape and the third lens L3 of a negative meniscus shape together. The number of lenses included in the entire lens system is three. The plane parallel plate P1 is positioned at the object side of the first lens L1, and the optical member PS is positioned at the image side of the cemented lens CE.

Basic lens data are shown in Table 1, and various items are shown in Table 2 for the objective lens for endoscopes of Example 1. In the lens data of Table 1, surface numbers i (i=1, 2, 3, . . . ) that sequentially increase toward the image side, with the surface toward the object side of the constituent element most toward the object side being designated as 1, are listed in the column Si; the radii of curvature of ith surfaces are listed in the column Ri; and distances along the optical axis Z between an ith surface and an i+1 st surface are listed in the column Di. In addition, refractive indices with respect to the d line (wavelength: 587.6 nm) of jth (j=1, 2, 3, . . . ) constituent elements, j sequentially increasing toward the image side with the constituent element most toward the object side being designated as 1, are listed in the column Ndj; and the Abbe's numbers with respect to the d line of jth constituent elements are listed in the column vdj.

Here, the signs of the radii of curvature are positive in cases that the shapes of the surfaces are convex toward the object side, and negative in cases that the shapes of the surfaces are concave toward the object side. Table 1 also shows data for the plane parallel plate P1, the aperture stop St, and the optical member PS. In Table 1, text reading "(St)" is indicated in the column for surface numbers along with the surface number for the surface that corresponds to the aperture stop St.

Table 2 shows the focal length f of the entire lens system, the back focus Bf of the entire lens system as an air converted distance, the F number F No., and the maximum full angle of view 2ω with respect to the d line. The symbol "(°)" in the column for 2ω indicates that the unit is degrees. The tables below show numerical values which are rounded off at a predetermined number of digits.

TABLE 1

| Example 1 | | | | |
|---|---|---|---|---|
| Si | Ri | Di | Ndj | vdj |
| 1 | ∞ | 0.343 | 1.88300 | 40.8 |
| 2 | ∞ | 0.143 | | |
| 3 | −0.960 | 0.844 | 1.89286 | 20.4 |
| 4 | −1.688 | 0.000 | | |
| 5 (St) | ∞ | 0.343 | | |
| 6 | 1.962 | 0.631 | 1.88300 | 40.8 |
| 7 | −0.960 | 0.400 | 1.89286 | 20.4 |
| 8 | −2.046 | 0.571 | | |
| 9 | ∞ | 1.143 | 1.51633 | 64.1 |
| 10 | ∞ | | | |

TABLE 2

| Example 1 | |
|---|---|
| f | 1.00 |
| Bf | 1.22 |
| F No. | 5.00 |
| 2ω (°) | 110.6 |

Diagrams that illustrate spherical aberration, astigmatism, distortion, and lateral chromatic aberration (chromatic aberration of magnification) of the objective lens for endoscopes of Example 1 are illustrated in this order from the left side of the drawing sheet in FIG. 4. The diagram that illustrates spherical aberration show aberrations related to the d line (wavelength: 587.6 nm), the C line (wavelength: 656.3 nm), and the F line (wavelength: 486.1 nm) as a solid line, a long broken line, and a short broken line, respectively. In the diagram that illustrates astigmatism, aberrations in the sagittal direction related to the d line are indicated by a solid line and aberrations in the tangential direction related to the d line are indicated by a short broken line, respectively. In the diagram that illustrates distortion, aberrations related to the d line are shown as a solid line. In the diagram that illustrates lateral chromatic diagram, aberrations related to the C line, and the F line are shown as a long broken line, and a short broken line, respectively. In the diagram that illustrates spherical aberration, "FNo." denotes the F number. In the other diagrams that illustrate the aberrations, ω denotes half angles of view. The aberrations illustrated in FIG. 4 are those for a case in which an object at a distance of 9.14 from the first surface shown in the basic lens data is being observed.

The symbols, the meanings, and the manner in which the data are shown in the diagrams related to Example 1 above are the same for the following Examples to be described later, unless particularly noted. Therefore, redundant descriptions will be omitted hereinbelow.

EXAMPLE 2

The lens configuration of and the paths of light beams that pass through the objective lens for endoscopes of Example 2 are illustrated in FIG. 2. The objective lens for endoscopes of Example 2 has, in order from the object side and the image side, a first lens L1 of a negative meniscus shape with a concave surface toward the object side, an aperture stop St, and a cemented lens CE formed by cementing a second lens L2 of a biconvex shape and a third lens L3 of a negative meniscus shape together. The number of lenses included in the entire lens system is three. A plane parallel plate P1 is positioned at the object side of the first lens L1, and a plane parallel plate P2 and an optical member PS are positioned at the image side of the cemented lens CE. The plane parallel plate P2 presumes a filter or the like.

Figure 5:
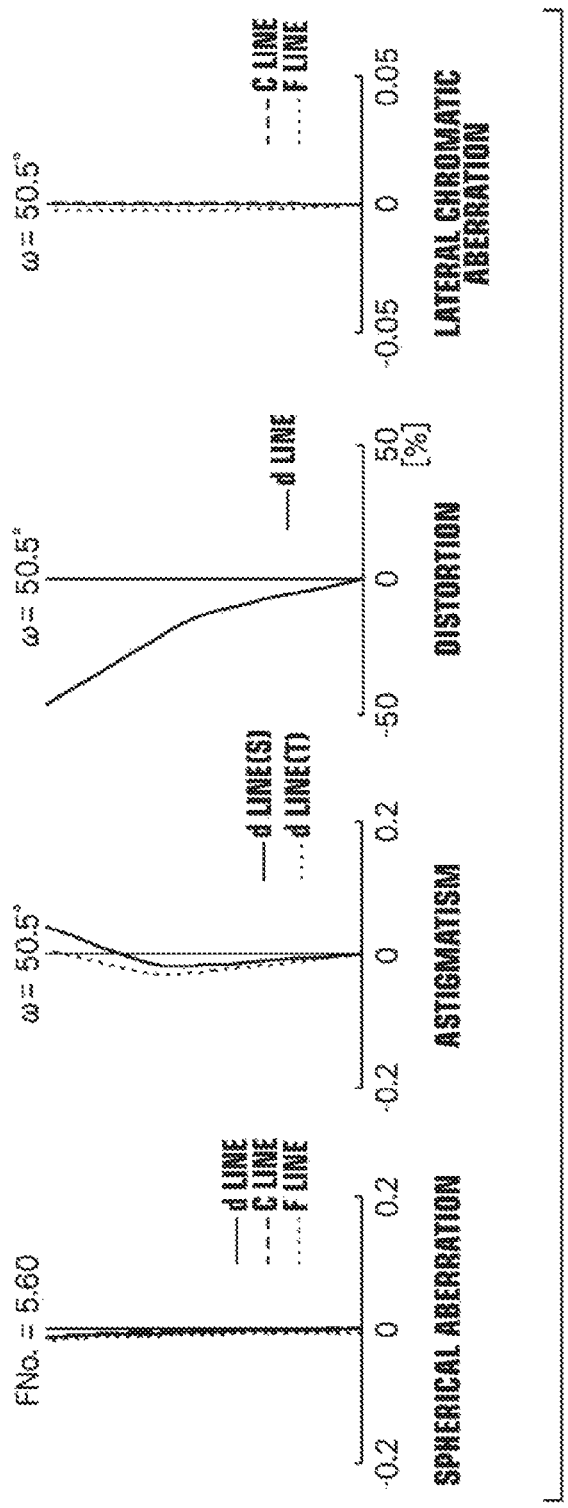
FIG. 5 is a collection of diagrams that illustrate various aberrations of the objective lens for endoscopes of Example 2, which are spherical aberration, astigmatism, distortion, and lateral chromatic aberration in this order from the left side of the drawing sheet.

Basic lens data are shown in Table 3, and various items are shown in Table 4 for the objective lens for endoscopes of Example 2. Aberration diagrams of the objective lens for endoscopes of Example 2 are illustrated in FIG. 5. The aberrations illustrated in FIG. 5 are those for a case in which an object at a distance of 8.47 from the first surface shown in the basic lens data is being observed.

TABLE 3

Example 2

| Si | Ri | Di | Ndj | vdj |
|---|---|---|---|---|
| 1 | ∞ | 0.318 | 1.88300 | 40.8 |
| 2 | ∞ | 0.133 | | |
| 3 | −0.847 | 1.152 | 1.90043 | 37.4 |
| 4 | −1.647 | 0.000 | | |
| 5 (St) | ∞ | 0.318 | | |
| 6 | 1.364 | 1.069 | 1.77250 | 49.6 |
| 7 | −1.228 | 0.318 | 1.95906 | 17.5 |
| 8 | −2.761 | 0.212 | | |
| 9 | ∞ | 0.212 | 1.51633 | 64.1 |
| 10 | ∞ | 0.302 | | |
| 11 | ∞ | 0.847 | 1.51633 | 64.1 |
| 12 | ∞ | | | |

TABLE 4

Example 2

| | |
|---|---|
| f | 1.00 |
| Bf | 1.12 |
| F No. | 5.60 |
| 2ω (°) | 101.0 |

EXAMPLE 3

The lens configuration of and the paths of light beams that pass through the objective lens for endoscopes of Example 3 are illustrated in FIG. 3. The objective lens for endoscopes of Example 3 has, in order from the object side and the image side, a first lens L1 of a negative meniscus shape with a concave surface toward the object side, an aperture stop St, and a cemented lens CE formed by cementing a second lens L2 of a negative meniscus shape and a third lens L3 of a biconvex shape together. The number of lenses included in the entire lens system is three. An optical member PS is positioned at the image side of the cemented lens CE.

Basic lens data are shown in Table 5, and various items are shown in Table 6 for the objective lens for endoscopes of Example 3. Aberration diagrams of the objective lens for endoscopes of Example 3 are illustrated in FIG. 6. The aberrations illustrated in FIG. 6 are those for a case in which an object at a distance of 9.20 from the first surface shown in the basic lens data is being observed.

TABLE 5

Example 3

| Si | Ri | Di | Ndj | vdj |
|---|---|---|---|---|
| 1 | −0.994 | 1.057 | 2.00330 | 28.3 |
| 2 | −2.079 | 0.000 | | |
| 3 (St) | ∞ | 0.345 | | |
| 4 | 1.963 | 0.345 | 1.95906 | 17.5 |
| 5 | 0.852 | 1.355 | 1.90043 | 37.4 |
| 6 | −1.914 | 0.575 | | |
| 7 | ∞ | 1.150 | 1.51633 | 64.1 |
| 8 | ∞ | | | |

TABLE 6

Example 3

| | |
|---|---|
| f | 1.00 |
| Bf | 1.24 |
| F No. | 4.00 |
| 2ω (°) | 120.0 |

Table 7 shows values corresponding to Conditional Formulae (1) through (6) for the objective lenses for endoscopes of Examples 1 through 3. The data shown in Table 7 are those with respect to the d line.

TABLE 7

| Formula | | Example 1 | Example 2 | Example 3 |
|---|---|---|---|---|
| (1) | dSt/Lt | 0.38 | 0.40 | 0.34 |
| (2) | vp − vn | 20.4 | 32.1 | 19.9 |
| (3) | fce/f | 1.30 | 1.50 | 1.40 |
| (4) | Lt/f | 2.22 | 2.86 | 3.10 |
| (5) | Bf/f | 1.22 | 1.12 | 1.24 |
| (6) | 2ω | 110.6 | 101.0 | 120.0 |

As can be understood from the above data, each of the objective lenses for endoscopes of Examples 1 through 3 are lens systems having three lens configurations, are compact, are configured to have wide angles with full angles of view of 100° or greater, favorably correct various aberrations including chromatic aberrations, and realize high optical performance.

Next, an embodiment of an endoscope to which the objective lens for endoscopes of the present disclosure is applied will be described with reference to FIG. 7. FIG. 7 illustrates the schematic structure of the entire endoscope. The endoscope 100 illustrated in FIG. 7 is mainly equipped with an operating portion 102, an insertion portion 104, and a universal cord 106 to be connected to a connector portion (not shown). The majority of the insertion portion 104 is a flexible portion 107 which can be bent in desired directions along an insertion path. A bendable portion 108 is linked to the leading end of the flexible portion 107, and a leading end portion 110 is linked to the leading end of the bendable portion 108. The bendable portion 108 is provided to orient the leading end portion 110 in desired directions. Bending operations are enabled by rotating a bending operation knob 109 provided on the operating portion 102. An objective lens 1 for endoscopes according to an embodiment of the present disclosure is provided within the interior of the leading end portion 110. Note that the objective lens for endoscopes 1 is schematically illustrated in FIG. 7. The endoscope of the present embodiment is equipped with the objective lens 1 for endoscopes. Therefore, miniaturization of the leading end portion 110 can be achieved, and favorable images having favorable color reproducibility.

The present disclosure has been described with reference to the embodiments and Examples. However, the present disclosure is not limited to the above embodiments and Examples, and various modifications are possible. For example, the values of the radii of curvature, the distances among surfaces, the refractive indices, the Abbe's numbers, and the aspherical surface coefficients of each lens are not limited to those exemplified in the above Examples, and may be different values.

What is claimed is:

1. An objective lens for endoscopes comprising, in order from the object side to the image side:
    a single lens having a negative refractive power and a concave surface toward the object side;
    an aperture stop; and
    a cemented lens;
    the cemented lens being formed by one positive lens and one negative lens which are cemented together;
    the number of lenses within the entire system being only three; and
    Conditional Formulae (1) and (2) below being satisfied:

$$0.1 < dSt/Lt < 0.6 \tag{1}$$

$$0 < vp - vn < 55 \tag{2}$$

wherein dSt is the distance along the optical axis from the surface toward the object side of the single lens to the aperture stop, Lt is the distance along the optical axis from the surface toward the object side of the single lens to the surface toward the image side of the cemented lens, vp is the Abbe's number with respect to the d line of the positive lens within the cemented lens, and vn is the Abbe's number with respect to the d line of the negative lens within the cemented lens.

2. An objective lens for endoscopes as defined in claim 1, in which Conditional Formula (3) below is satisfied:

$$1.0 < fce/f < 2.0 \tag{3}$$

wherein fce is the focal length of the cemented lens, and f is the focal length of the entire lens system.

3. An objective lens for endoscopes as defined in claim 1, in which Conditional Formula (4) below is satisfied:

$$1.5 < Lt/f < 5.0 \tag{4}$$

wherein f is the focal length of the entire lens system.

4. An objective lens for endoscopes as defined in claim 1, in which Conditional Formula (5) below is satisfied:

$$0.8 < Bf/f < 1.8 \tag{5}$$

wherein Bf is the back focus of the entire lens system as an air converted distance, and f is the focal length of the entire lens system.

5. An objective lens for endoscopes as defined in claim 1, in which Conditional Formula (6) below is satisfied:

$$90° < 2\omega \tag{6}$$

wherein $2\omega$ is the maximum full angle of view.

6. An objective lens for endoscopes as defined in claim 1, in which Conditional Formula (1-1) below is satisfied:

$$0.2 < dSt/Lt < 0.5 \tag{1-1}$$

7. An objective lens for endoscopes as defined in claim 1, in which Conditional Formula (2-1) below is satisfied:

$$10 < vp - vn < 45 \tag{2-1}$$

8. An objective lens for endoscopes as defined in claim 2, in which Conditional Formula (3-1) below is satisfied:

$$1.1 < fce/f < 1.7 \tag{3-1}$$

9. An objective lens for endoscopes as defined in claim 2, in which Conditional Formula (3-2) below is satisfied:

$$1.2 < fce/f < 1.6 \tag{3-2}$$

10. An objective lens for endoscopes as defined in claim 3, in which Conditional Formula (4-1) below is satisfied:

$$1.8 < Lt/f < 4.0 \tag{4-1}$$

11. An objective lens for endoscopes as defined in claim 4, in which Conditional Formula (5-1) below is satisfied:

$$1.0 < Bf/f < 1.5 \tag{5-1}$$

12. An objective lens for endoscopes as defined in claim 5, in which Conditional Formula (6-1) below is satisfied:

$$100° < 2\omega \tag{6-1}$$

13. An objective lens for endoscopes as defined in claim 1, further comprising:
    a plane parallel plate positioned at the most object side thereof.

14. An endoscope equipped with an objective lens for endoscopes as defined in claim 1.

* * * * *